United States Patent [19]

Bowden et al.

[11] 4,108,856

[45] Aug. 22, 1978

[54] CHLORINATION PROCESS FOR PRODUCING 2,3,5-TRICHLOROPYRIDINE

[75] Inventors: Roy Dennis Bowden; Thomas Seaton, both of Runcorn, England

[73] Assignee: Imperial Chemical Industries Limited, London, England

[21] Appl. No.: 845,389

[22] Filed: Oct. 25, 1977

[30] Foreign Application Priority Data

Oct. 26, 1976 [GB] United Kingdom .............. 44408/76

[51] Int. Cl.$^2$ .......................................... C07D 213/04
[52] U.S. Cl. .......................................... 260/290 HL
[58] Field of Search .............................. 260/290 HL

[56] References Cited

U.S. PATENT DOCUMENTS

| 3,251,848 | 5/1966 | Taplin | 260/290 HL |
| 3,420,833 | 1/1969 | Taplin | 260/290 HL |
| 3,555,032 | 1/1971 | Johnston | 260/290 HL |
| 3,557,124 | 1/1971 | Stringham et al. | 260/290 HL |

*Primary Examiner*—Alan L. Rotman
*Attorney, Agent, or Firm*—Cushman, Darby & Cushman

[57] ABSTRACT

2,3,5-Trichloropyridine is prepared by the vapor phase chlorination of 3,5-dichloropyridine.

6 Claims, No Drawings

CHLORINATION PROCESS FOR PRODUCING 2,3,5-TRICHLOROPYRIDINE

This invention relates to a chlorination process, and more particularly to a process for the preparation of 2,3,5-trichloropyridine.

It is known that a variety of polychloropyridines may be obtained by the vapour phase chlorination of pyridine or substituted pyridines.

In the specification of U.K. Pat. No. 1,041,906 there is described a process for the manufacture of substituted pyridines containing one or more chlorine atoms as substituents in the pyridine ring which comprises interacting pyridine or a substituted pyridine with chlorine in the vapour phase at elevated temperature. The process described therein is especially applicable to the vapour-phase chlorination of pyridine itself, in which case high yields of pentachloropyridine may be obtained; pentachloropyridine is also the product when 2-chloropyridine is the starting material.

In the specification of U.S. Pat. No. 3,420,833 the product of a vapour-phase chlorination of pyridine is described as comprising 2,4,6-trichloropyridine; 2,3,4,6-tetrachloropyridine; 2,3,6-trichloropyridine and 2,3,5,6-tetrachloropyridine with minor proportions of pentachloropyridine and 2,6-dichloropyridine.

2,3,5-trichloropyridine does not appear to be produced in any significant proportion either by the chlorination of pyridine itself or by the chlorination of monochloropyridines.

We have now found that 2,3,5-trichloropyridine may be produced in good yield provided that the starting material is a specific dichloropyridine, namely 3,5-dichloropyridine.

Thus according to the present invention there is provided a process for the production of 2,3,5-trichloropyridine which comprises interacting 3,5-dichloropyridine with chlorine in the vapour phase at an elevated temperature.

The chlorination process is preferably carried out at a temperature in the range from 300° C to 460° C. A temperature in the range from 340° to 400° (for example 380° C) is especially preferred.

It is preferred to preheat separately the feed of chlorine and the feed of 3,5-dichloropyridine.

The reactants are preferably diluted. The diluent may be inorganic, for example nitrogen and/or steam, or may be organic.

When an organic diluent is used, this is preferably a compound which is inert towards chlorine (for example carbon tetrachloride, which is the diluent especially preferred) or a compound such that any reaction with chlorine yields a product which is inert to further chlorination (for example chloroform, which may yield carbon tetrachloride.

When a gaseous or volatile diluent is used the chloropyridine starting material may be vapourised in the stream of diluent vapour which serves as a carrier gas; when a liquid diluent is used, the 3,5-dichloropyridine starting material may be dissolved in the liquid diluent and the resulting solution may then be vaporised as a whole.

It is preferred to use at least 1 mole of chlorine per mole of 3,5-dichloropyridine. It is especially preferred to use at least 2 moles of chlorine (for example from 5 to 15 moles of chlorine) per mole of 3,5-dichloropyridine.

When using a diluent which is reactive towards chlorine, for example chloroform, an appropriate additional amount of chlorine may be used to allow for that consumed by reaction with the diluent.

Convenient residence times of the mixture in the reaction zone are, for example, between 10 and 30 seconds, but higher or lower residence times may also be used if desired.

2,3,5-trichloropyridine may be separated from any other chloropyridines produced by methods conventional in the art, for example fractional distillation and fractional crystallisation.

2,3,5-trichloropyridine is useful as an intermediate for the manufacture of compounds of the formula (I)

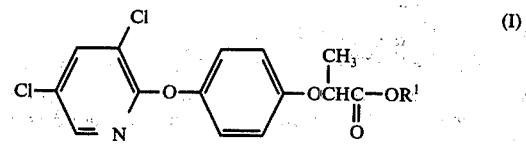

wherein R is a hydrogen atom or an alkyl group of 1 to 4 carbon atoms. Such compounds, and their salts, are useful as selective herbicides for the control of grass weeds, as set forth for example in Belgian Pat. No. 834,495.

2,3,5-trichloropyridine may be coverted into a compound of the formula (I) for example by reaction with a phenol derivative of formula:

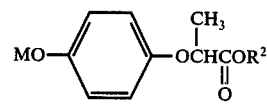

wherein $R^2$ is an alkyl group of 1 to 4 carbon atoms and M is an alkali metal, for example sodium or potassium to give a compound of formula (I) above.

The invention is illustrated by the following Examples:

EXAMPLE 1

A solution of 3,5-dichloropyridine (10g) in chloroform (55 ml) was fed to a packed vaporiser maintained at a temperature of 300° C to 310° C. The issuing vapours were passed to a vertical glass tubular reactor of 1 inch bore held at a temperature of 380° where they were mixed with chlorine fed at a rate of 0.2 liter/minute (measured at 20° C). The residence time was 22 seconds. The initial reaction mixture contained 6.6 moles of chlorine per mole of 3,5-dichloropyridine.

The gaseous reactor effluent was condensed and collected in cooled carbon tetrachloride. The resulting carbon tetrachloride solution was distilled to remove carbon tetrachloride, and the residual solid recrystallised from acetic acid. The product thus obtained was analysed by gas-liquid chromatography and nuclear mass spectroscopy. 50% of the 3,5-dichloropyridine fed was converted into 2,3,5-trichloropyridine.

EXAMPLE 2

The general procedure was similar to that described in Example 1. The 3,5-dichloropyridine was dissolved in carbon tetrachloride and the reactor was a glass tubular reactor of 3.8 inch bore. The reaction conditions and the products obtained are summarized in the Table. The conversions shown are based upon 3,5-dichloropyridine fed.

TABLE

| Example | moles per mole 3,5-dichloropyridine | | reaction temperature °C | residence time sec. | % conversion | | |
|---|---|---|---|---|---|---|---|
| | $Cl_2$ | $CCl_4$ | | | unreacted 3,5-dichloropyridine | 2,3,5-trichloropyridine | 2,3,5,6-tetrachloropyridine |
| 2 | 6.41 | 9.55 | 336 | 16 | 49 | 51 | 0 |
| 3 | 6.46 | 9.64 | 380 | 15 | 11 | 75 | 14 |
| 4 | 6.46 | 9.61 | 400 | 15 | 0 | 49 | 51 |
| 5 | 9.26 | 10.3 | 370 | 18 | 8 | 70 | 22 |
| 6 | 2.87 | 11.5 | 375 | 11 | 24 | 60 | 16 |

What is claimed is:

1. A process for the production of 2,3,5-trichloropyridine which comprises interacting 3,5-dichloropyridine with chlorine at a temperature in the range from 300° C to 460° C.

2. A process according to claim 1 wherein the reaction is carried out at a temperature in the range from 340° C to 400° C.

3. A process according to claim 1 wherein the proportion of chlorine is at least 1 mole per mole of 3,5-dichloropyridine.

4. A process according to claim 3 wherein the proportion of chlorine is at least 2 moles per mole of 3,5-dichloropyridine.

5. A process according to claim 4 wherein the proportion of chlorine is from 5 to 15 moles per mole of 3,5-dichloropyridine.

6. A process according to claim 1 wherein the reaction is carried out in the presence of a diluent from the group consisting of chloroform and carbon tetrachloride.

* * * * *